United States Patent [19]
Cubb et al.

[11] Patent Number: 5,287,848
[45] Date of Patent: Feb. 22, 1994

[54] EASY INTUBATOR

[76] Inventors: Anthony Cubb, 4301 Avila Ct., Arlington, Tex. 76003; Natalie Landy, 801 15th St., S. #508, Arlington, Va. 22202

[21] Appl. No.: 64,677

[22] Filed: May 21, 1993

Related U.S. Application Data

[63] Continuation-in-part of Ser. No. 767,873, Sep. 30, 1991, abandoned.

[51] Int. Cl.$^5$ .............................................. A61M 16/00
[52] U.S. Cl. .................................. 128/200.26; 128/11
[58] Field of Search ............................... 128/6, 10–13, 128/16, 18, 22, 200.26

[56] References Cited

U.S. PATENT DOCUMENTS

| | | | |
|---|---|---|---|
| 2,843,112 | 7/1958 | Miller | 128/6 |
| 4,126,127 | 11/1978 | May | 128/11 |
| 4,211,234 | 7/1980 | Fisher | 128/200.26 |
| 4,244,362 | 1/1981 | Anderson | 128/200.26 |
| 4,337,763 | 7/1982 | Petrassevich | 128/11 X |
| 4,425,909 | 1/1984 | Rieser | 128/13 X |
| 4,638,792 | 1/1987 | Burgin | 128/6 |
| 4,832,020 | 5/1989 | Augustine | 128/10 X |
| 4,901,708 | 2/1990 | Lee | 128/6 X |
| 4,905,669 | 3/1990 | Bullard et al. | 128/11 |
| 4,947,829 | 8/1990 | Bullard | 128/11 |
| 4,947,896 | 8/1990 | Bartlett | 128/11 |
| 5,003,963 | 4/1991 | Bullard et al. | 128/11 |

*Primary Examiner*—Vincent Millin
*Assistant Examiner*—Sebastiano Passaniti

[57] ABSTRACT

The invention depicts an instrument for medical use which facilitates and simplifies elective or emergency endotracheal intubation, to be used when indicated for ventilatory support. The invention consists of a one piece instrument, inclusive of an upper handle portion and curved lower blade portion made of a hard plastic material, fully disposable if desired, which allows suction capabilities as well as direct visualization of the vocal cords and larynx for accurate endotracheal intubation. The endotracheal tube is preloaded into one of the bored chambers of the embodiment of the invention. In addition, a second port is available which may be connected at the top of the device to equipment for suctioning, eliminating the need for a suction catheter. Direct visualization of the vocal cords, larynx, and upper airways is accomplished through fiberoptic bundles which bring the images to an eyepiece at the top handle portion of the device. The endotracheal tube can be safely advanced from a close proximity to the upper airways, through the vocal cords, followed by inflation of the balloon located in the endotracheal tube cuff. The plastic intubator may be slipped in an upward direction over the endotracheal tube, removed, and discarded. The process of intubation is completed and accomplished under direct visualization of anatomical structures throughout the procedure. Benefits are increased rapidity, minimal trauma, accuracy, enhanced safety, and minimal operator training. Further eliminated are the trial and error characteristics of blind procedures.

14 Claims, 4 Drawing Sheets

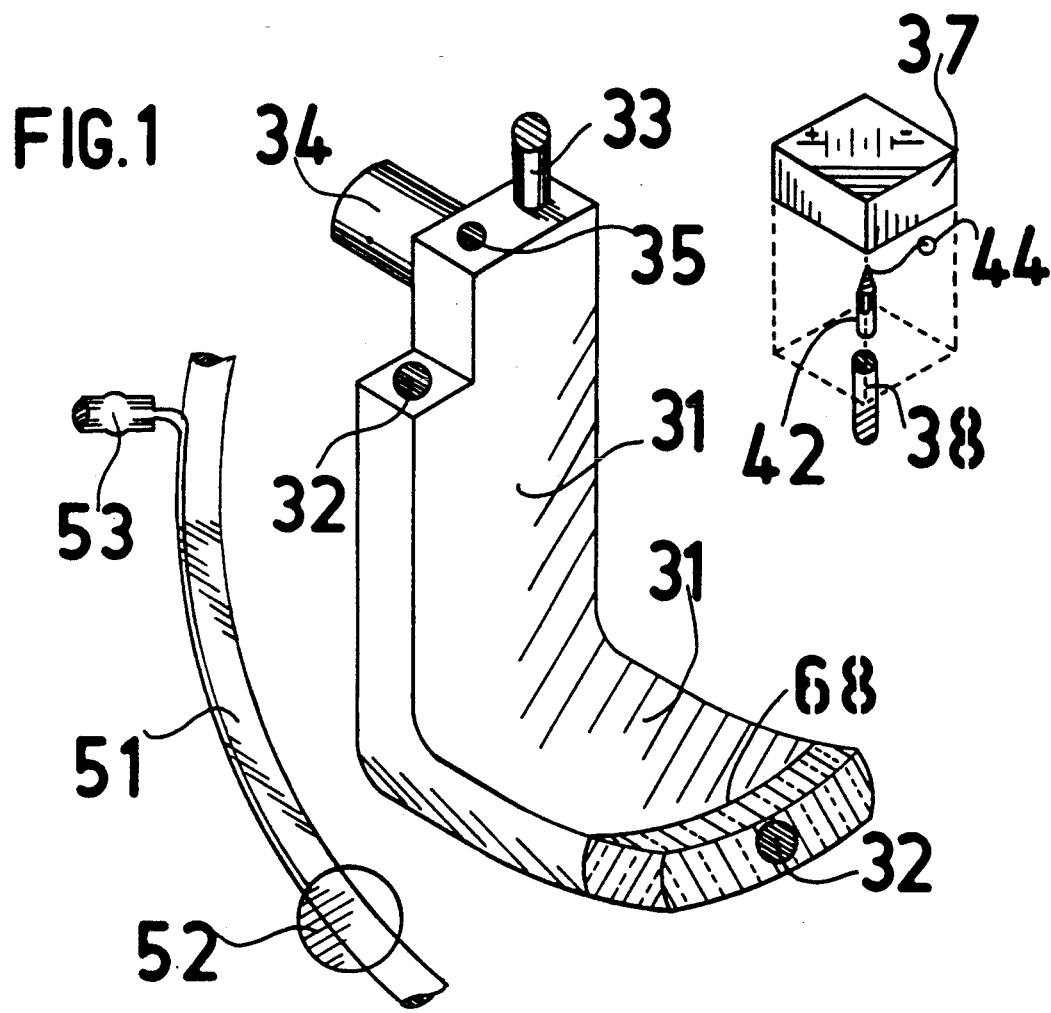
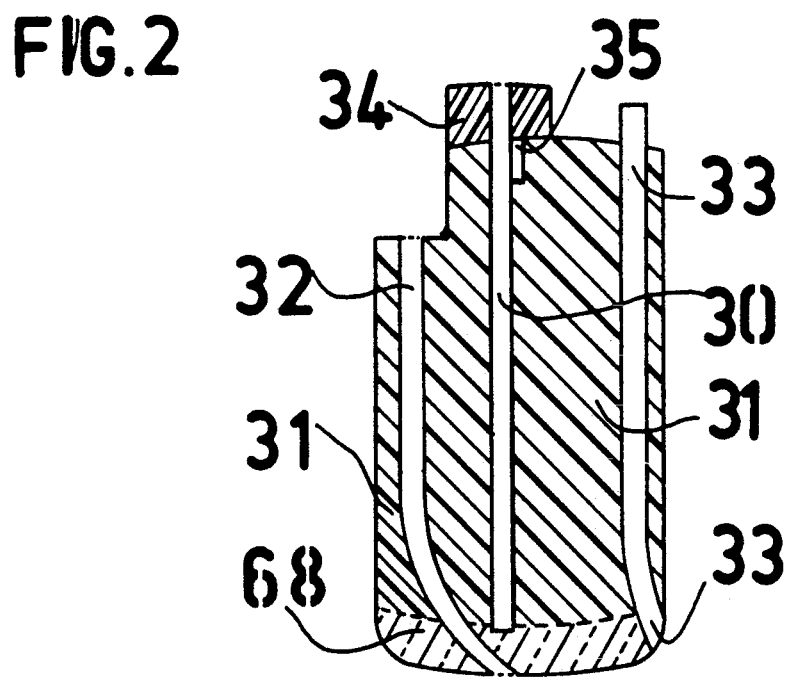

EASY INTUBATOR

This application is a continuation-in-part of application Ser. No. 07/767/873, filed Sep. 30, 1991, now abandoned.

BACKGROUND OF THE INVENTION

Examples of prior known intubator devices are shown in U.S. Pat. Nos. 5,038,766; 2,433,705; 2,854,004; and 4,947,896.

SUMMARY OF THE INVENTION

The invention refers to an instrument for medical use in endotracheal intubation during elective or emergency indications for ventilatory support. Endotracheal intubation is a procedure which requires a plastic, flexible tube to be passed through the nasal or oral cavity in a downward direction through the vocal cords and into the trachea. This procedure is performed during circumstances which require ventilatory support such as anesthesia during surgical procedures, trauma, and severe respiratory failure. Endotracheal intubation requires the use of a laryngoscope for visualization of anatomical structures. This is not always accomplished, requiring blind endotracheal intubation based on trial and error. This procedure carries high risk of injury to the vocal cords and adjacent anatomical structures. Failed attempts can be frequent and require a high degree of training to safely perform the procedure of intubation. The invention consists of a curved, one piece, disposable, hard plastic structure which embodies channels for suctioning, direct viewing of anatomical structures involved in endotracheal intubation, and a channel which houses a preloaded endotracheal tube. The end of the endotracheal tube, to be placed in the trachea is located at the lower end of the invention. Once the anatomical structures are visualized through the device, the endotracheal tube may be advanced through the vocal cords into the trachea, which is the desired area of placement.

The Easy Intubator consists of a curved, single unit, the upper portion being used as a handle, and the angled lower portion being used as a blade which gently lifts the base of the tongue in an upward direction to obtain direct visualization of the upper airways and vocal cords.

The Easy Intubator provides channels which extend downward through the length of the device. One channel can be used for suctioning of secretions, eliminating the necessity of a suction catheter, to enable enhanced direct visualization of the anatomical structures involved. A second channel holds an endotracheal tube which can be advanced with little effort through the vocal cords when direct visualization is obtained. With the use of this invention, endotracheal intubation can be accomplished under direct visualization of the anatomical structures in a safe, direct, easy, and rapid manner minimizing complications. Once endotracheal intubation is accomplished, the device may be removed by retracting the entire body of the device upward over the endotracheal tube, which securely remains in the desired location in the trachea. The preloaded endotracheal tube projects upward from the device allowing upward removal of the intubator while maintaining placement of the endotracheal tube in the trachea. The intubator may then be discarded.

The illuminating system of the invention may be powered by either a battery or electrical source and includes a light source, which attaches to a connecting port located at the upper end of the handle portion of the device. The area is illuminated and provides better visualization of the anatomical structures involved. Fiberoptic bundles enable transmission of light and images from the end of the device to the viewing portion of the invention.

BRIEF DESCRIPTION OF THE DRAWINGS

The features and advantages of this invention will be further clarified by the description as follows, accompanied by drawings wherein:

FIG. 1 is a front view of the one piece intubator showing an upper handle portion and a lower blade portion which houses three bored internal channels: a preloaded endotracheal tube, suction capability, and light source connection, respectively. An eyepiece is located in the upper back of the upper handle portion. Depicted in this figure is an endotracheal tube with an inflatable balloon and its mechanism for inflation. Also shown is a light-power supply source.

FIG. 2 is an idealized inner view of the channels described in FIG. 1.

FURTHER DISCUSSION OF THE INVENTION REFERENCING THE DRAWINGS

Figure 3:
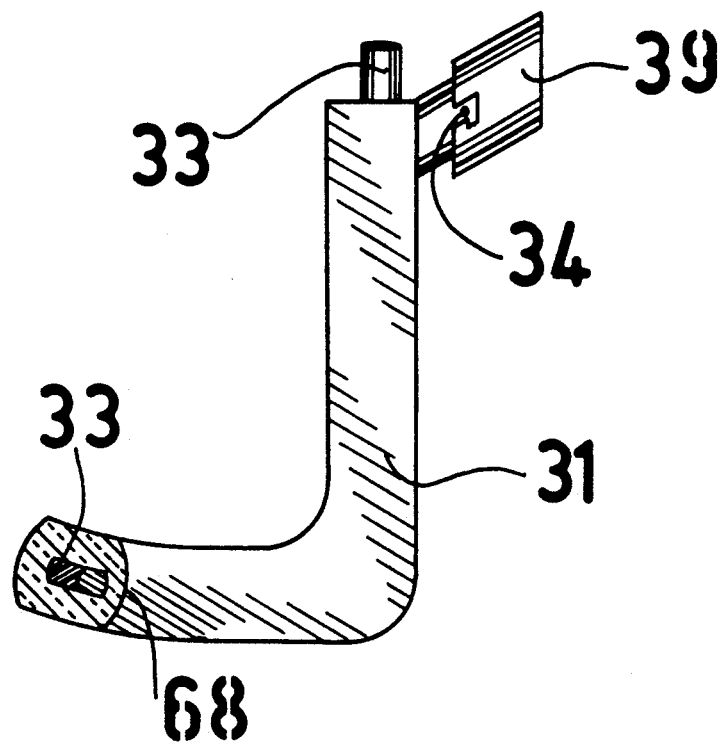
FIG. 3 is a side view of the invention showing the upper handle, eyepiece, and lower blade portion with the beginning opening of the suction channel.

Referring to FIG. 1, there is shown a front view of the curved, one piece, hard plastic intubator which has an upper handle portion and a lower blade portion 31. An open port 33 runs from the bottom of the intubator, through the intubator, to the top of the intubator handle. Direct suction may be applied to the top port 33, eliminating the need for suction catheters. A small port 35 for the connection of a light source 42 powered by either a power cell 37 or external source 44 is provided. A lateral recessed port 32 runs the length of the device and centrally exits the end of the lower blade portion 31. The recessed bored channel 32 accomodates endotracheal tube 51,52,53 which may be prepositioned in channel 32 for direct intubation. An eyepiece 34 carries the distal image through fiber bundle strands upward to the eyepiece, which is angled anatomically to provide ease of visualization of the vocal cords and allows direct visual access for safe and certain intubation by advancing the preloaded endotracheal tube 51 down through the vocal cords into the trachea.

Figure 6:
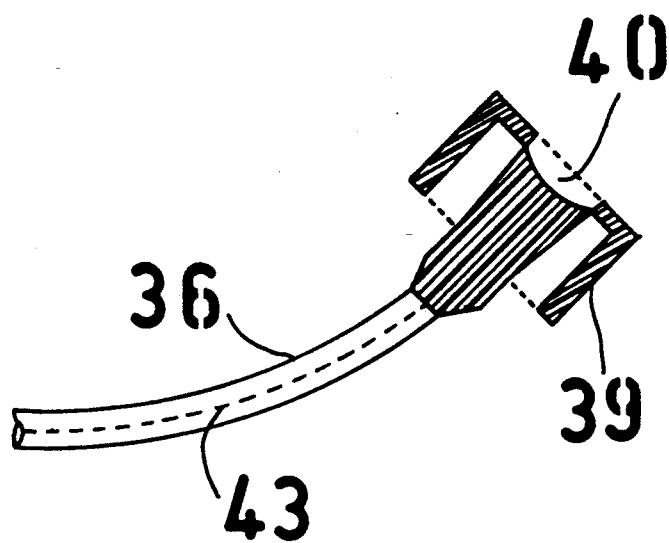
FIG. 6 is a cross section of the structure shown in FIG. 5, showing the location of the fiberoptic bundle, and the electrical conduction structure of the device.

Referring to FIG. 2, there is shown an cross-sectional view of the intubating device shown in FIG. 1. FIG. 2 shows a channel for suctioning 33 which runs the length of the device, beginning at the the top of the handle of the invention 31 to the opening at the lower end portion of the blade of the invention 31. This channel 33 permits suctioning of foreign material and secretions from the throat when suction is applied to the upper opening of the channel, eliminating the need for a suction catheter. A recessed channel 32, located toward the side of the device, accomodates a long, preloaded, commercially available endotracheal tube 51, as shown in FIG. 1. The preloaded endotracheal tube 51 with an inflatable cuff 52 and cuff inflating valve mechanism 53 is located centrally in close proximity to the end of the channel 32. A port 35 for the connection of a light 42 and a power source 37 for illumination of the throat and vocal cords, using a battery or electrical source, 37, as shown in FIG. 1, is provided. The extension 38 which connects the light to the fiberoptic system of the device is shown. A cross-sectional view of the eyepiece 34 is illustrated. The eyepiece 34 serves as a means of visualizing anatomical structures during the intubation procedure. The image is carried from near the end of the channel 30 upward through the fiberoptics to the eyepiece 34, which is located at the upper end of the device. Images and light are carried back from the end of the device to the eyepiece 34 by fiberoptic bundles. The fibers 43, as shown in FIG. 6, are surrounded by a sheath and are located within a channel 30 of the embodiment of the device and end a short distance from the end of the blade portion. The fibers and light source enable direct visualization of the anatomical structures, which are necessary to visualize during endotracheal intubation. The distal portion 20 of the blade 31 is constructed of transparent plastic to facilitate light dispersion into the surrounding areas.

Referring to FIG. 3, a side view is shown of the curved device 31, eyepiece 34, snap-on eyepiece cover 39, and the lower end of the suction channel 33. The eyepiece cover 39 contains a lens for visualization of images collected at the end of the blade portion, as described in FIG. 2.

Figure 4:
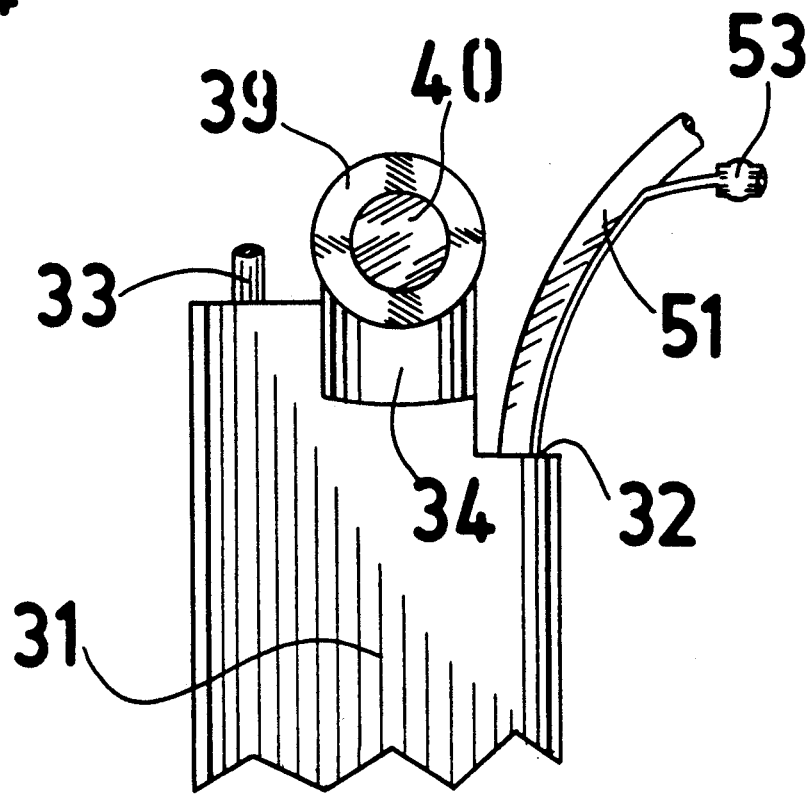
FIG. 4 is a rear view of the upper portion of the invention showing eyepiece, viewer lens structures, and suction channel. The recessed portion shows a preloaded endotracheal tube.

Referring to FIG. 4, a rear view is shown of the upper portion of the handle 31, eyepiece 34, and snap-on eyepiece cover 39 containing a lens 40. The lens 40 serves as a screen to visualize images of anatomical structures at the end portion of the device. The lens 40 is contained within the snap-on eyepiece cover 39. A suction connecting port 33 and a recessed portion housing an endotracheal tube 51 is shown.

Figure 5:
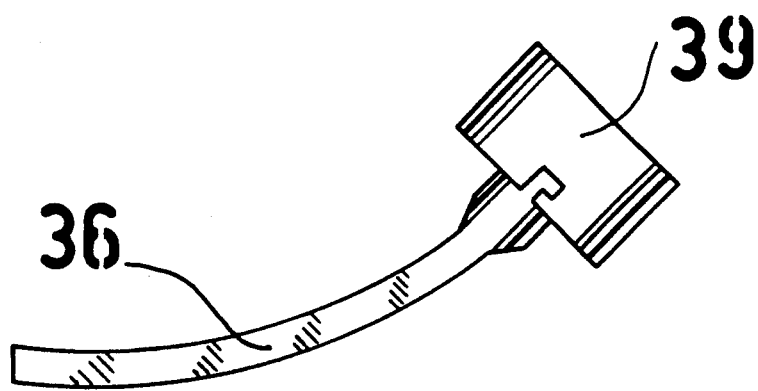
FIG. 5 is a side view of the snap-on eyepiece portion and external sheath carrying fiberoptics and light to the end portion of the device.

Referring to FIG. 5, a side view is shown of the snap-on eyepiece portion and external sheath which carries the fiberoptics, power source, and light to the end portion of the device. A sheath 36 covers the fiber bundles 43, shown in FIG. 6. The sheath and its contents are attached to the snap-on eyepiece cover 39. The sheath and its contents are introduced into the channel 30, as shown in FIG. 2, which is provided in the embodiment of the device for the purpose of illuminating the anatomical structures. The eyepiece cover 39 can be easily disassembled to be removed as a unit, consisting of the lens 40, and the fiberoptics 43, contained within the sheath 36, as shown in FIG. 6. This unit may be reused.

Referring to FIG. 6, a cross section of the structures described in FIG. 5 are shown. Structures include a cross section of the snap-on lens cover 39, lens 40, fiberoptic bundle 43, and covering sheath 36.

Figure 7:
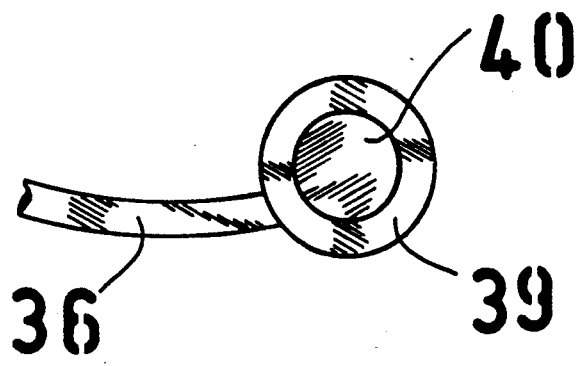
FIG. 7 is a top view of the structures depicted in FIG. 5.

Referring to FIG. 7, a top view of the structures depicted in FIG. 5 are shown. A snap-on eyepiece cover 39 contains a lens which serves as a screen for images received from the fiberoptics. A protective sheath 36 encloses and surrounds the fiberoptics 43, as shown in FIG. 6.

Figure 8:
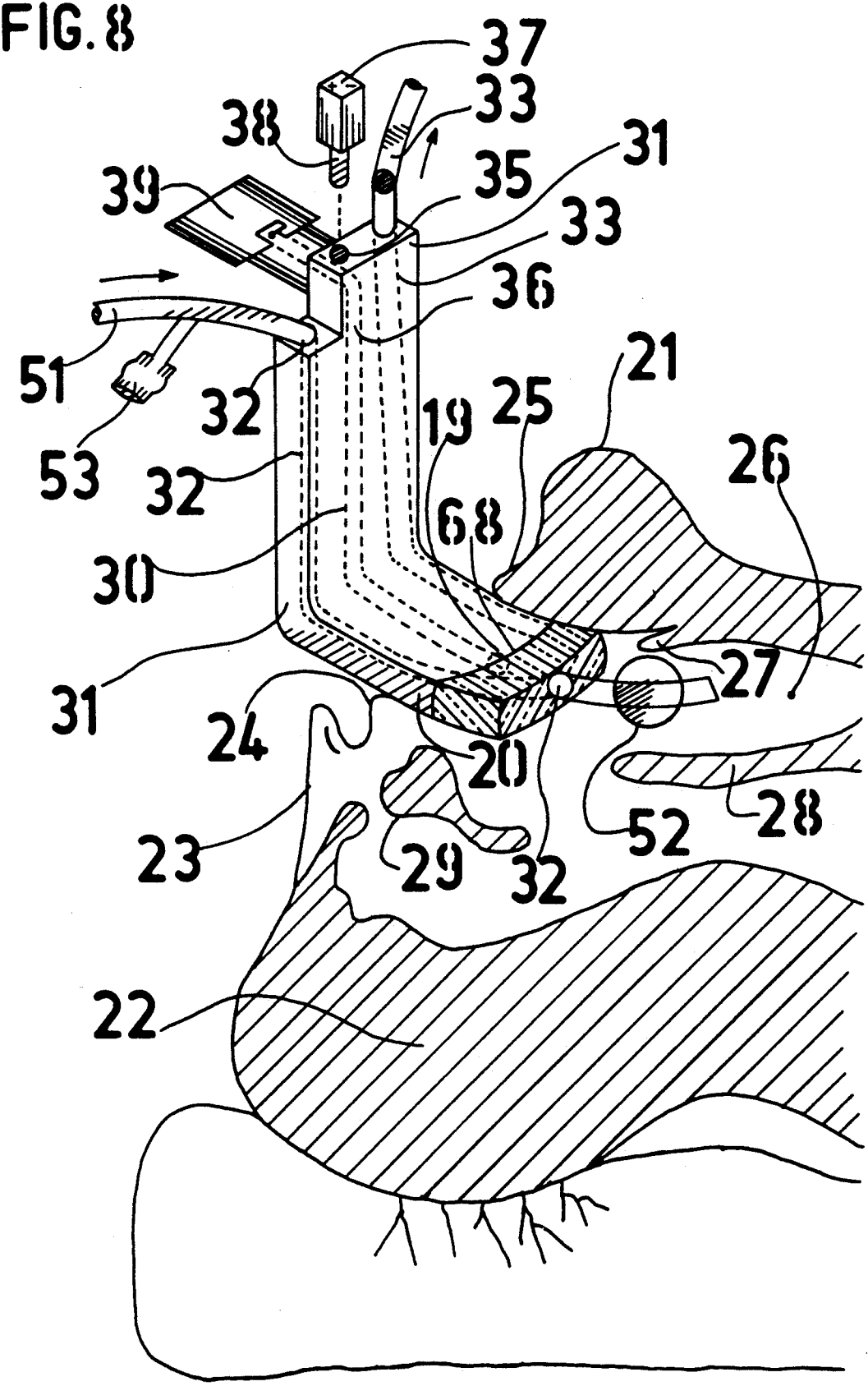
FIG. 8 is an environmental view of the subject intubation device.

Referring to FIG. 8, the intubation device of the present invention is shown entering the human larynx area and passes the roof of the mouth 29, the epiglottis 27, the vocal cords 28, and into the larynx and trachea 26, as shown by the arrow. The endotracheal tube is advanced, upon intubation, along with the intubator, through the mouth to the epiglottis, where the vocal cords are directly visualized. The endotracheal tube is then advanced slightly, through the focal cords and larynx and into the trachea, where the cuffed endotracheal tube balloon is inflated. The intubator allows for direct visualization throughout the entire intubation procedure. The endotracheal tube can then be held at the top portion of the tube and the intubator can be pulled back up and over the length of the endotracheal tube and discarded after intubation is complete. The cut-away portion of the intubator allows the operator to grasp the endotracheal tube and aid the inflated balloon to hold the tube in place while the intubator is being retracted following completion of the intubation process. The fiber optic bundles terminate at 19 within the transparent distal portion 20 of the intubator, allowing continuous and direct visualization of the pathway of the endotrachael tube to observe the anatomical structures therein. Transmitted light enters the channel portion 35 and, upon intubation, illuminates the anatomical structures, with the resulting image being viewed by the operator through the ascending fiber optic bundles to the eyepiece, covered by the eyepiece cover 39.

While the present invention has been described with reference to specifics, it will be understood that changes may be made and substituted while maintaining the scope of the invention. Modifications may also be made to adapt to a situation, size, composition of material, or desirability of structure without departing from its inherent characteristics of practicality, safety, and speed of use of the device.

What is claimed is:

1. An intubation guide for the easy and accurate positioning of an endotracheal tube through the vocal cords of a patient being intubated, comprising:
   an upper handle portion;
   a lower blade portion joined to the upper handle portion for inserting into the patient's mouth;
   a plurality of spaced conduits longitudinally extending from the upper portion into the lower portion of said guide;
   one of the conduits being adapted to removeably receive the endotracheal tube therein, said conduit extending the entire length of said lower blade portion and penetrating a terminal edge of said lower blade portion;
   a second conduit being adapted to be connected to a suction source, said second conduit penetrating a terminal edge of said lower blade portion to remove fluids from within the patient's mouth;
   a third conduit being adapted to both receive a light source for illuminating the area into which the endotrachael tube is to be positioned and receive receiving images from the illuminated area, said third conduit terminating within said lower blade portion to prevent contact with the patient's bodily fluid; and an eyepiece positioned in the upper handle portion cooperatively connected to said third conduit for viewing the patient's throat.

2. The intubation guide of claim 1 and further including a light source removeably positioned in said third conduit for illuminating the patient's throat.

3. The intubation guide of claim 1 formed of plastic.

4. The intubation guide of claim 3 wherein the first and third conduits are disposed at an acute angle with respect to each other at the distal portion whereby a tip of the endotracheal tube can be readily observed by the viewer as it is moved into operational position.

5. The intubation guide of claim 1 wherein the first and third conduits are disposed at an angle with respect to each other at the distal portion whereby a tip of the endotrachael tube can be readily observed by the viewer as it is moved into operational position.

6. The intubation guide of claim 1, wherein the third conduit includes a fiber optic bundle for transmitting light out of said lower blade portion and a fiber optic bundle for receiving and transmitting images to said eyepiece to enable the proper positioning of the endotrachael tube.

7. The intubation guide of claim 6 wherein the first and third conduits are disposed at an acute angle with respect to each other at the distal portion whereby a tip of the endotracheal tube can be readily observed by the viewer as it is moved into operational position.

8. The intubation guide of claim 6 wherein said fiber optic bundle is permanently positioned in said third conduit.

9. The intubation guide of claim 10 wherein said guide is formed of plastic.

10. The intubation guide of claim 9 wherein the first and third conduits are disposed at an acute angle with respect to each other at the distal portion, whereby a tip of the endotracheal tube can be readily observed by the viewer as it is moved into operational position.

11. The intubation guide of claim 10 and further including a light source removeably positioned in said third conduit for illuminating the patient's throat.

12. The intubation guide of claim 8 wherein the first and third conduits are disposed at an acute angle with respect to each other at the distal portion whereby a tip of the endotracheal tube can be readily observed by the viewer as it is moved into operational position.

13. The intubation guide of claim 6 wherein said fiber optic bundle terminates within the distal end of said guide, said distal end being made of transparent material to permit observation of the guide pathway via the fiber optic bundle.

14. The intubation guide of claim 13 wherein the first and third conduits are disposed at an acute angle with respect to each other at the distal portion whereby a tip of the endotracheal tube can be readily observed by the viewer as it is moved into operational position.

* * * * *